US008879816B2

(12) United States Patent
Inoue (10) Patent No.: US 8,879,816 B2
(45) Date of Patent: Nov. 4, 2014

(54) ULTRASONIC DIAGNOSTIC APPARATUS AND ULTRASONIC IMAGE DISPLAY METHOD

(75) Inventor: Shinsuke Inoue, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 109 days.

(21) Appl. No.: 13/821,797

(22) PCT Filed: Jul. 28, 2011

(86) PCT No.: PCT/JP2011/067191
§ 371 (c)(1),
(2), (4) Date: Mar. 8, 2013

(87) PCT Pub. No.: WO2012/039193
PCT Pub. Date: Mar. 29, 2012

(65) Prior Publication Data
US 2013/0177229 A1 Jul. 11, 2013

(30) Foreign Application Priority Data
Sep. 21, 2010 (JP) ................................. 2010-211163

(51) Int. Cl.
| G06K 9/00 | (2006.01) |
| A61B 8/14 | (2006.01) |
| A61B 8/00 | (2006.01) |
| A61B 8/08 | (2006.01) |
| G06T 11/00 | (2006.01) |
| G06T 15/08 | (2011.01) |

(52) U.S. Cl.
CPC ................. *G06T 11/003* (2013.01); *A61B 8/14* (2013.01); *A61B 8/466* (2013.01); *G06T 2210/41* (2013.01); *A61B 8/483* (2013.01); *G06T 15/08* (2013.01); *A61B 8/485* (2013.01); *A61B 8/5223* (2013.01)
USPC .......................................... 382/131; 382/154

(58) Field of Classification Search
CPC .......... A61B 8/14; A61B 8/466; A61B 8/483; A61B 8/5223; A61B 8/485; G06T 11/003; G06T 15/08; G06T 2210/41
USPC ................................. 382/100, 128–132, 154
See application file for complete search history.

(56) References Cited

U.S. PATENT DOCUMENTS 7,520,855 B2 * 4/2009 Tamano et al. ............... 600/437
2007/0112270 A1 5/2007 Waki et al.
(Continued)

FOREIGN PATENT DOCUMENTS

| JP | A-2000-60853 | 2/2000 |
| JP | A-2008-259605 | 10/2008 |

(Continued)

OTHER PUBLICATIONS

International Search Report issued in International Patent Application No. PCT/JP2011/067191 dated Oct. 25, 2011 (w/translation).

(Continued)

*Primary Examiner* — Shefali Goradia
(74) *Attorney, Agent, or Firm* — Oliff PLC (57) ABSTRACT

Provided is an ultrasonic diagnostic apparatus capable of clearly depicting areas of noteworthy hardness. In order to clearly depict 3-dimensional elasticity images of the area of noteworthy hardness, frequency is counted for each magnitude of the elasticity value for the elasticity data configuring the volume data, and elasticity values in a prescribed range which is determined on the basis of frequency, are converted to be large and elasticity values outside the prescribed range are converted to be small. By rendering the post-conversion volume data, the large elasticity values of areas of noteworthy hardness are integrated and 3-dimensional elasticity images are generated.

13 Claims, 8 Drawing Sheets

(56) References Cited

U.S. PATENT DOCUMENTS

| | | |
|---|---|---|
| 2010/0324421 A1 | 12/2010 | Waki et al. |
| 2011/0178404 A1 | 7/2011 | Waki |
| 2012/0163124 A1* | 6/2012 | Akiyama et al. ................ 367/87 |

FOREIGN PATENT DOCUMENTS

| JP | A-2008-284287 | 11/2008 |
|---|---|---|
| JP | A-2009-240464 | 10/2009 |
| WO | WO 2005/048847 A1 | 6/2005 |
| WO | WO 2010/026823 A1 | 3/2010 |

OTHER PUBLICATIONS

Office Action issued in Chinese Application No. 201180045185.2 issued Jun. 30, 2014.

* cited by examiner

FIG.8 the present invention to a 3-dimensional image.

ULTRASONIC DIAGNOSTIC APPARATUS AND ULTRASONIC IMAGE DISPLAY METHOD

FIELD OF THE INVENTION

The present invention relates to an ultrasonic diagnostic apparatus which uses ultrasonic waves to display an ultrasonic image of a diagnostic region in an object to be examined, and more particularly, to an ultrasonic diagnostic apparatus capable of displaying an elasticity image representing the hardness of a living organ of the object as a 3-dimensional image.

DESCRIPTION OF RELATED ART

As described in Patent Documents 1 and 2, a conventional ultrasonic diagnostic apparatus transmits ultrasonic waves into an object, receives the ultrasonic reflected echo signal of a living organ from the reflected wave, performs signal processing on the signal to generate and display a black and white tomographic image (B-mode image) of a diagnostic region having the reflectance as its luminance.

Patent Document 2 has disclosed a technique involving performing 3-dimensional coordinate conversion from the black and white tomographic image and its acquired position to obtain 3-dimensional volume data including a plurality of tomographic image data sets arranged 3-dimensionally and then performing volume rendering thereof to provide a black and white 3-dimensional image of a diagnostic region viewed from an arbitrary direction of line of sight. A disclosed technique of the rendering includes providing an opacity for each of voxels constituting the 3-dimensional volume data in accordance with the value of the luminance of the voxel, sequentially accumulating the luminance values of the voxels on the line of sight until the accumulated value of the opacities of the voxels arranged on the line of sight reaches one, and using the accumulated luminance value as a pixel value on a 2-dimensional projection plane.

Patent Documents 1 and 2 have also disclosed a technique of determining an elasticity image of a diagnostic region. First, two frames of the black and white tomographic image are selected, block matching or the like is performed to determine the displacement of each point on the image between the two frames, the determined displacement is subjected to known calculations to determine the elasticity value (such as strain and coefficient of elasticity) representing the hardness for each point on the image. The magnitude of the determined elasticity value is converted into hue information based on a color conversion table to obtain the 2-dimensional elasticity image representing the elasticity value as the hue.

In addition, Patent Document 2 has disclosed a technique in which, in order to solve the problem of being incapable of obtaining a 3-dimensional image of an inner lesion portion hidden by outer voxels having high opacities in a 3-dimensional gray-scale image, an opacity is provided for each of the voxels in the 3-dimensional volume data obtained from the black and white tomographic image in accordance with the magnitude of the elasticity value to perform volume rendering. This can provide the 3-dimensional gray-scale image showing a hard organ more opaquely and a soft organ more transparently.

In Patent Document 2, a plurality of 2-dimensional elasticity images are coordinate-converted into 3-dimensional volume data which is then subjected to volume rendering to produce a 3-dimensional elasticity image. In the typical rendering method in which voxel values are simply accumulated, a problem occurs in which the elasticity values are accumulated to provide the 3-dimensional elasticity image including distorted elasticity characteristics of a living organ, so that the luminance data of the black and white tomographic image is used to determine the voxel having the highest contribution on the line of sight, and the elasticity value of that voxel is used as the elasticity value of the 2-dimensional projection plane to generate the 3-dimensional elasticity image.

For the display method, the black and white tomographic image (2-dimensional) and the 2-dimensional elasticity image are displayed one on the other in Patent Document 1. In Patent Document 2, the black and white 3-dimensional image and the 3-dimensional elasticity image are superimposed into one image which is then displayed together with the black and white tomographic images in three directions on one screen.

Patent Document 3 has disclosed displaying a black and white tomographic image and a 2-dimensional elasticity image together on one screen and superimposing and displaying the black and white tomographic image on the 2-dimensional elasticity image.

PRIOR ART REFERENCES

Patent Documents

Patent Document 1: WO2005/048847
Patent Document 2: JP-A-2008-259605
Patent Document 3: JP-A-2000-60853

SUMMARY OF THE INVENTION

Technical Problems

In the conventional method for obtaining an elasticity image of an object, as described in Patent Documents 1 and 2, a black and white tomographic image of two frames is selected and the amount of displacement between the two frames caused by applied pressure is acquired in the respective points on an image, so as to obtain the elasticity value (strain, elasticity modulus, etc.) on the basis of the acquired displacement.

In this manner, the elasticity value becomes large in biological tissue which is soft and subjected to a large amount of distortion and the elasticity value becomes small in biological tissue which is hard and subjected to a small amount of distortion.

Though often the tissue that an operator seeks to clearly observe is hard tissue such as a tumor, the elasticity value of hard tissue is small, and the elasticity value of the soft tissue which covers the hard tissue is large. The conventional volume rendering method for generating 3-dimensional gray-scale images includes providing an opacity for each of the voxels constituting the 3-dimensional volume data in accordance with the value of the luminance of the voxel, sequentially accumulating the luminance values of the voxels on the line of sight until the accumulated value of the opacities of the voxels arranged on the line of sight reaches one, and using the accumulated luminance value as a pixel value on a 2-dimensional projection plane. For this reason, if the volume rendering method is applied to the rendering of volume data of an elasticity value, the contribution rate of the voxels which is soft and have a large elasticity value to a 2-dimensional projection plane becomes high, whereby making it difficult to display a noteworthy hard tissue which is inside of a soft tissue.

If the data of the voxel in soft tissue having a large elasticity value is removed by means such as filtering, though a 3-dimensional image of the voxels of hard tissue can be obtained, since the elasticity values of the hard tissue's are small and the integrated value by rendering also becomes small, thus it is hard to obtain a clear 3-dimensional image with high contrast.

While the technique disclosed in Patent Document 2 performs rendering to obtain a 3-dimensional image of a lesion which is hidden inside soft tissue by providing opacity to the respective voxels of the 3-dimensional volume data which is acquired from a black and white tomographic image according to the magnitude of the elasticity value, a 3-dimensional elasticity image cannot be obtained from doing so since the integrated value to be calculated by this technique is the luminance data (ultrasonic reflectivity) of a black and white tomographic image.

The objective of the present invention is to provide the ultrasonic diagnostic apparatus capable of clearly depicting a 3-dimensional elasticity image of a region having a noteworthy hardness.

BRIEF SUMMARY OF THE INVENTION

In order to achieve the above-described objective, in accordance with the present invention, the following ultrasonic diagnostic apparatus will be provided. The ultrasonic diagnostic apparatus comprises:

an elasticity image volume data creating unit configured to create volume data from the elasticity value data which shows the elasticity using the signal received by transmitting an ultrasonic wave to the inside of an object;

an elasticity value converting unit configured to count the frequency for every magnitude of elasticity value with respect to the elasticity value data which constitutes volume data for each magnitude of the elasticity value, and converts the elasticity values within a prescribed range which is determined based on the frequency into a large value and the elasticity values outside the prescribed range into a small value; and a volume rendering unit configured to generate a 3-dimensional elasticity image by rendering the post-conversion volume data by the elasticity value converting unit.

Also, another aspect of the present invention provides the method of displaying ultrasonic images. The display method of ultrasonic images generates and displays a 3-dimensional elasticity image by generating the volume data constituted by the elasticity value data showing the elasticity using the signal received by transmitting an ultrasonic wave to the inside of an object, counting the frequency by each magnitude of the elasticity value with respect to the elasticity value data that constitute volume data, converting the elasticity values within a prescribed range which is determined based on the frequency into a large value and the elasticity values outside the prescribed range into a small value, and rendering the post-conversion volume data.

EFFECT OF THE INVENTION

In accordance with the present invention, in the case of integrating the elasticity values by volume rendering, the elasticity value which is determined by the frequency in the region having a noteworthy hardness becomes large, whereby making it possible to generate a 3-dimensional elasticity image having a large contrast in the region with noteworthy hardness.

BRIEF DESCRIPTION OF THE DRAWINGS

FIG. 3($a$) is a graph in the first embodiment showing the relationship between the elasticity value generated by the elasticity value converting unit and the frequency, and ($b$) is a graph in the first embodiment showing the relationship between the post-conversion elasticity value (relative value) in the elasticity value converting unit and the elasticity value (relative value) before the conversion.

FIG. 4($a$) is an explanatory diagram showing a screen example in which a 3-dimensional elasticity image obtained in the first embodiment and a composite image of a 2-dimensional elasticity image and a black and white tomographic image are displayed, ($b$) is an enlarged view of a color map 15 in ($a$), and ($c$) is an explanatory diagram showing a screen example in which a 3-dimensional elasticity image of a comparative example and a composite image of a 2-dimensional elasticity image and a black and white tomographic image are displayed.

FIG. 5($a$) is a graph in a second embodiment showing the relationship between the elasticity values generated in the elasticity value converting unit and the frequency, and ($b$) is a graph in the second embodiment showing the relationship between the post-conversion elasticity values (relative value) in the elasticity values converting unit and the pre-conversion elasticity value (relative value).

FIG. 7($a$) is a graph in a third embodiment showing the relationship between the elasticity value generated by the elasticity value converting unit and the frequency, and ($b$) is a graph in the third embodiment showing the relationship between the post-conversion elasticity value (relative value) in the elasticity value converting unit and the elasticity value (relative value) before the conversion.

FIG. 8($a$) is a graph in a fourth embodiment showing the relationship between the elasticity value generated in the elasticity value converting unit and the frequency, and ($b$) is a graph in the fourth embodiment showing the relationship between weight w generated by the elasticity value converting unit and the elasticity value (relative value) before the conversion.

DETAILED DESCRIPTION OF THE INVENTION

The ultrasonic diagnostic apparatus in an embodiment of the present invention will be described below referring to the attached diagrams. In the present embodiment, a B-mode image showing the distribution of the ultrasonic reflection of tissue in a predetermined cross-section of an object is referred to as a black and white tomographic image, a 2-dimensional projection image in which the volume data constituted by the data of a black and white tomographic image is rendered is referred to as a 3-dimensional image, an image showing the 2-dimensional distribution in a predetermined cross-section of the elasticity value that represents the elasticity of tissue in the object is referred to as a 2-dimensional elasticity image, and a 2-dimensional projection image in which the volume data constituted by the data of a 2-dimensional elasticity image is rendered is referred to as a 3-dimensional elasticity image.

Figure 1:
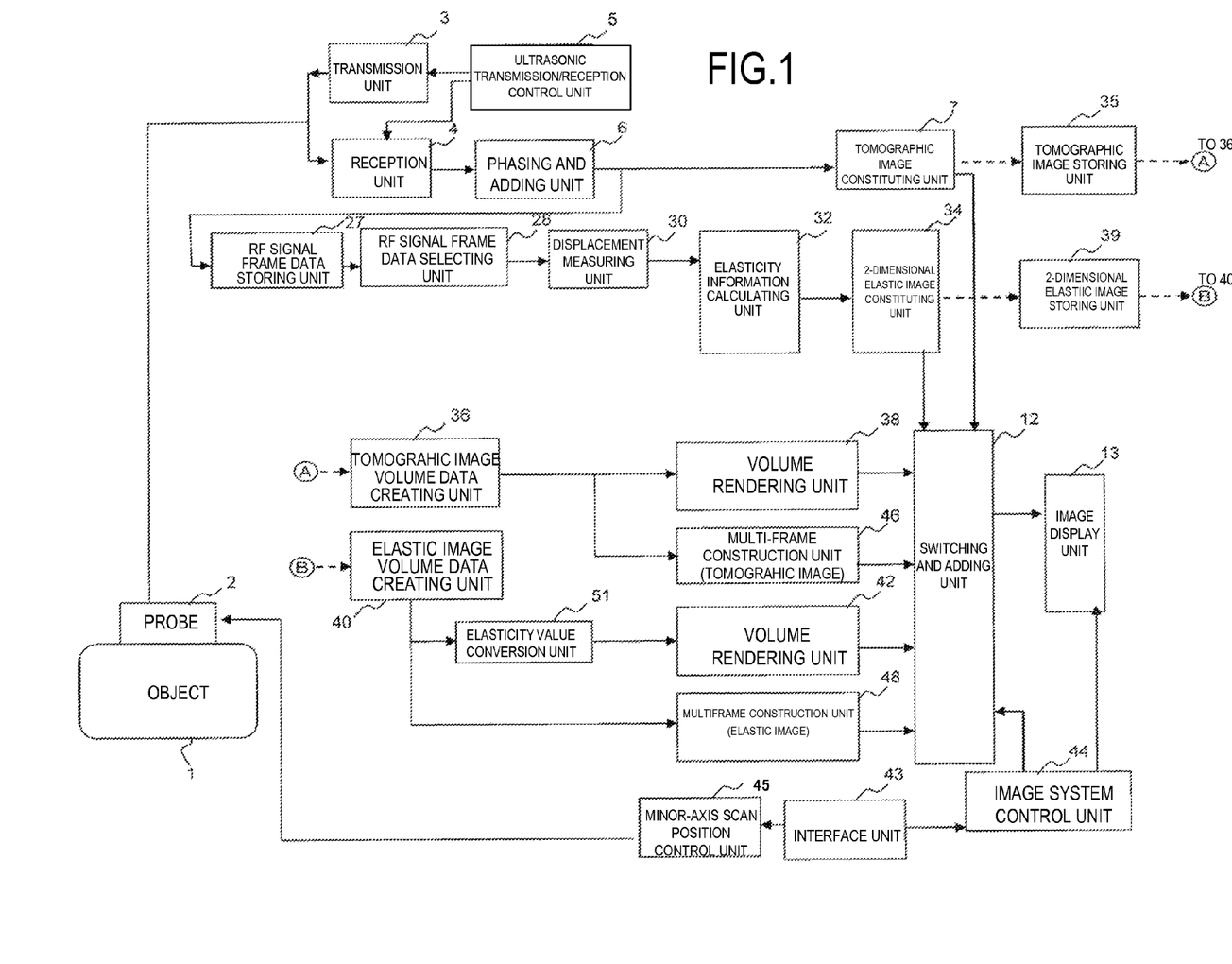
FIG. 1 is a block diagram showing the configuration of the ultrasonic diagnostic apparatus of an embodiment.

As shown in FIG. 1, the ultrasonic diagnostic apparatus comprises a probe 2 to be used by applying to an object 1, a transmission unit 3 configured to repeatedly transmit ultrasonic waves to a diagnostic region in the object 1 via the probe 2 at predetermined intervals, a reception unit 4 configured to receive the reflected echo signals reflected from the object 1 in the time series, an ultrasonic transmission/reception control unit 5, and a phasing and adding unit 6 configured to perform phasing and adding of the received reflected echoes.

The probe 2 includes plural transducers arrayed in a linear or sector form, and ultrasonic waves are transmitted and received between the transducers and the object 1. The probe 2 is provided with a function to mechanically scan plural transducers in the direction orthogonal to the array direction thereof (minor-axis direction), thus is capable of 3-dimensionally transmitting and receiving ultrasonic waves. The ultrasonic probe 2, by using the type in which plural transducers are 2-dimensionally arrayed, may have the configuration capable of 3-dimensionally transmitting and receiving ultrasonic waves without mechanically oscillating the transducers.

The transmission unit 3 generates a transmission pulse for producing ultrasonic waves by driving the probe 2. At that time, it controls the phase of the transmission signal to be transferred to the respective transducers of the probe 2, and sets the conversion point of the transmitted ultrasonic waves at a certain depth. Also, the reception unit 4 generates an RF signal, i.e. a reception signal by amplifying the reflected echo signal received by the respective transducers of the probe 2 at a predetermined gain. The ultrasonic transmission/reception control unit 5 controls devices such as the transmission unit 3 and the reception unit 4. The phasing and adding unit 6 generates RF signal frame data (which is equivalent to RAW data) by phasing and adding the phase of the RF signals and forming an ultrasonic beam which is converged with respect to one or plural conversion points.

Also, the ultrasonic diagnostic apparatus comprises an interface unit 43 configured to receive the setting from an operator, an image display unit 13, a switching and adding unit 12 configured to switch the kind of images to be displayed on the image display unit 13, an image system control unit 44 and a minor-axis scan position control unit 45. The minor-axis scan position control unit 45 performs 3-dimensional transmission and reception in a predetermined range by controlling the operation of the probe 2 to be mechanically scanned in the direction orthogonal to the array direction of the plural transducers.

Further, the ultrasonic diagnostic apparatus further comprises, as the configuration for generating from RF frame data a black and white tomographic image and a 3-dimensional image of a diagnostic region having the ultrasonic reflection as the luminance, a tomographic image constructing unit 7, a tomographic image storing unit 35, a tomographic image volume data creating unit 36, a volume rendering unit 38 and a multi-frame constructing unit (tomographic image) 46. In addition, as the configuration for generating from RF frame data a 2-dimensional elasticity image and a 3-dimensional elasticity image, it comprises an RF signal frame data storing unit 27, an RF signal frame data selecting unit 28, a displacement measuring unit 30, an elasticity information calculating unit 32, an elasticity image constructing unit 34, a 2-dimensional elasticity image storing unit 39, an elasticity image volume data creating unit 40, a volume rendering unit 42, a multi-frame constructing unit (elasticity image) 48 and an elasticity value converting unit 51.

The tomographic image constructing unit 7 performs processing such as gain compensation, log compression, detection, edge enhancement and filtering with respect to the RF signal frame data generated in the phasing and adding unit 6, and generates a black and white tomographic image (B-mode image) of a diagnostic region having the reflection rate as the luminance (shading). At that time, the image system control unit 44 receives the condition for generating black and white tomographic images from the operator via the interface unit 43, and controls the tomographic image constructing unit 7.

The tomographic image storing unit 35 subjects the black and white tomographic image constructed by the tomographic image constructing unit 7 to correspond with its acquiring position and stores them. The acquiring position here means the moving distance in the minor-axis direction under control of the minor-axis scan position control unit 45. The volume data creating unit 36 creates 3-dimensional volume data by performing coordinate conversion which rearranges the plural black and white tomographic images (for one volume) stored in the tomographic image storing unit 35 in accordance with the moving direction in the minor-axis direction.

The volume rendering unit 38 constructs a 3-dimensional image (a 2-dimensional projection image of 3-dimensional volume data) of a diagnostic region in an object by volume rendering the 3-dimensional volume data generated by the volume data creating unit 36 on the basis of the luminance and opacity using the following expressions (1)~(3). The projection direction (line-of-sight direction) is received from an operator by the image system control unit 44 via the interface 43.

$$C\text{out}(i) = C\text{out}(i-1) + (1 - A\text{out}(i-1)) \cdot A(i) \cdot C(i) \cdot S(i) \qquad \text{expression (1)}$$

$$A\text{out}(i) = A\text{out}(i-1) + (1 - A\text{out}(i-1)) \cdot A(i) \qquad \text{expression (2)}$$

$$A(i) = B\text{opacity}[C(i)] \qquad \text{expression (3)}$$

In the expression (1), Cout(i) represents the value output as the pixel value of the 2-dimensional projection plane. C(i) represents the luminance value of an i-th voxel (where i=0 to N−1) present on the line of sight when the 3-dimensional image is viewed from a certain point on the 2-dimensional projection plane. The voxel refers to the position of each of luminance data sets constituting the 3-dimensional volume data. When N voxels are arranged on the line of sight, the luminance value Cout(N−1) calculated by accumulating the luminance values of the voxels (i=0 to N−1) with the expression (1) is the pixel value to be output finally. Cout(i−1) represents the accumulated value up to an (i−1)-th voxel.

A(i) in the expression (1) represents the opacity of the i-th voxel present on the line of sight and takes values ranging from 0 to 1.0. The opacity A(i) is determined in accordance with the magnitude of the luminance value of the voxel by referencing a table (Bopacity[C(i)] defining the predefined relationship between luminance value C(i) and opacity or by substituting the luminance value C(i) into a function (Bopacity[C(i)] defining the predefined relationship between the luminance value C(i) and opacity as shown in the expression (3). For example, a higher opacity is provided for a voxel having a higher luminance value. The opacity thus provided in accordance with the luminance value determines the contribution rate of the luminance value C(i) of the voxel to the luminance value Cout(N−1) of the 2-dimensional projection plane to be output.

Aout(i) in the expression (2) is the value calculated by accumulating the opacities A(i) provided from the expression (3) in accordance with the right side of the expression (2) up to the i-th voxel. In the expression (1), the accumulated value Aout(i−1) of the opacities up to the (i−1)-th voxel calculated as in the expression (2) is used. As apparent from the expression (2), Aout(i) is accumulated each time the voxel is passed, and is converged to 1.0. Thus, when the accumulated value Aout(i−1) of the opacities up to the (i−1)-th voxel is approximately 1.0 as shown in the above expression (1), the second term in the right side of the expression (1) is 0, and the luminance value C(i) of the i-th and subsequent voxels is not reflected in the 2-dimensional projection image (3-dimensional) to be output. The initial values of Cout(i) and Aout(i) are zero.

S(i) in the expression (1) is a weight component for shading and is calculated from the slope of the luminance value determined from the luminance value C(i) and its surrounding luminance values. For example, when the normal line to the plane centered on the ith voxel (slope of the luminance value) matches the optical axis of a predefined light source, the light is reflected most strongly and thus 1.0 is provided as S(i) for the voxel i based on a predefined table and function. When the light source is orthogonal to the normal line, 0.0 is provided as S(i). This s provides the shading for the obtained 2-dimensional projection image to achieve a highlighting effect.

The multi-frame constituting unit (tomographic image) 46 generates a black and white tomographic image on an arbitrary cross-section from the 3-dimensional volume data created by the volume data creating unit 36. The position of the arbitrary cross-section is received by the interface unit 43 from the operator and is set in the multi-frame constituting unit (tomographic image) 46 through the image system control unit 44. A plurality of positions of the arbitrary cross-sections may be set, and the multi-frame constituting unit 46 generates the black and white tomographic image for each of the plurality of positions of the arbitrary cross-sections.

With such configurations, a 3-dimensional image and a black and white tomographic image in an arbitrary section of the diagnostic region in the object 1 are formed.

The RF signal frame data produced by the phasing and adding unit 6 is sequentially stored in the RF signal frame data storage unit 27. For example, the RF signal frame data storage unit 27 sequentially stores the RF signal data produced on the time series, that is, on the basis of the frame rate of the image, from the phasing and adding unit 6 in a frame memory. The RF signal frame data selecting unit 28 selects a set, that is, two sets of RF signal frame data from the plural sets of RF signal frame data stored in the RF signal frame data storage unit 27. For example, in response to an instruction from the image system control unit 44, the RF signal frame data selecting unit 28 selects the last stored RF signal frame data (N) as first data, and selects one set of RF signal frame data (X) from a group of RF signal frame data (N−1, N−2, N−3, ..., N−M) stored previously. N, M, and X represent index numbers provided for the RF signal frame data sets and are natural numbers.

The displacement measuring unit 30 determines a displacement or the like of a living organ from a set of RF signal frame data.

For example, the displacement measuring unit 30 performs 1-dimensional or 2-dimensional correlation processing on the set of data, that is, the RF signal frame data (N) and the RF signal frame data (X) selected by the RF signal frame data selecting unit 28 to determine 1-dimensional or 2-dimensional displacement distribution for a displacement and a movement vector (direction and magnitude of displacement) in the living organ for each point in the tomographic image (2-dimensional reflectivity image). A block matching method is used for detecting the movement vector. The block matching method includes dividing the tomographic image into blocks each constituting of N pixels by N pixels, for example, focusing on a block within a region of interest, searching the previous frame for a block having the reflectivity distribution most approximate to that of the focused block, and referencing that block to determine a sample value through predictive coding, that is, differences.

The elasticity information calculating unit 32 performs predetermined calculations based on the displacement and the movement vector determined by the displacement measuring unit 30 to calculate the elasticity value and outputs it as time-series elasticity frame data. The elasticity value mentioned herein may be a value representing the elasticity of the organ of the object 1, and examples thereof include strain, coefficient of elasticity, displacement, viscosity, strain ratio and the like. When the strain is used as the elasticity value, it can be calculated by spatial differentiation of the movement amount of the living organ such as displacement.

The 2-dimensional elasticity image constituting unit 34 includes a frame memory and an image processing unit, and stores the elasticity frame data output on the time series from the elasticity information calculating unit 32 in the frame memory and processes the stored frame data in the image processing unit to produce the 2-dimensional elasticity image representing the 2-dimensional distribution of the elasticity values in the diagnostic region of the object. The 2-dimensional elasticity image is a color image provided by converting the elasticity values into hue information based on a predefined color conversion table. For example, as the elasticity value is changed from a predetermined small value toward a larger value, the hue is given in 255 levels (1 to 255) gradually changing from blue (B) to green (G), and then red (R). The elasticity value at the hardest part is one, and the elasticity value at the softest part is 255.

The 2-dimensional elasticity image storage unit 39 matches and stores the 2-dimensional elasticity image produced in the elasticity image constituting unit 34 and its acquired position. The volume data creating unit 40 performs 3-dimensional coordinate conversion based on the 2-dimensional elasticity image stored in the 2-dimensional elasticity image storage unit 39 and its acquired position to produce 3-dimensional volume data including the plurality of spatially contiguous 2-dimensional elasticity images placed 3-dimensionally.

The elasticity information converting unit 51 converts the elasticity value that constitutes 3-dimensional volume data in order to obtain a 3-dimensional image so that the shape of tissue having a noteworthy hardness for an operator, for example hard tissue with a small elasticity value can be distinctly recognized. In this manner, the 3-dimensional volume data is generated showing the tissue having a noteworthy hardness with a large elasticity value and soft tissue with a small elasticity value. The conversion method will be concretely described later in the first~fourth embodiments.

The volume rendering unit 42 renders the elasticity volume data converted by the elasticity value converting unit 51 using the following expressions (4)~(6). The projection direction (line-of-sight direction) is received by the image system control unit 44 from the operator via the interface 43. In this manner, a 3-dimensional elasticity image regarding the voxels of tissue having a noteworthy hardness (post-conversion large elasticity value range) for the operator can be obtained, whereby making it possible to identify the 3-dimensional shape of hard tissue covered by soft tissue.

$$E\text{out}(i) = E\text{out}(i-1) + (1 - A\text{out}(i-1)) \cdot A(i) \cdot E(i) \cdot S(i) \qquad (4)$$

$$A\text{out}(i) = A\text{out}(i-1) + (1 - A\text{out}(i-1)) \cdot A(i) \qquad (5)$$

$$A(i) = E\text{opacity}[E(i)] \qquad (6)$$

In the expression (4), Eout(i) represents the value output as the pixel value of the projection plane. E(i) represents the elasticity value of an i-th voxel (where i=0 to N−1) present on the line of sight after the voxel is converted (the post-conversion elasticity value by the elasticity value converting unit 51) when the 3-dimensional elasticity image is viewed from a certain point on the 2-dimensional projection plane. When the elasticity values of N voxels are arranged on the line of sight, the accumulated value Eout(N−1) calculated by accumulating the elasticity values (i=0 to N−1) with the expression (4) is the pixel value to be output finally. Eout(i−1) represents the accumulated value up to the (i−1)-th voxel.

A(i) in the expression (4) represents the opacity of the i-th voxel present on the line of sight and takes values ranging from 0 to 1.0. The opacity AU) is determined in accordance with the magnitude of the elasticity value of the voxel by referencing a table (Eopacity[E(i)] defining the predefined relationship between elasticity value E(i) and opacity or by substituting the elasticity value E(i) into a function (Eopacity [E(i)] defining the predefined relationship between the elasticity value E(i) and opacity.

Aout(i) in the expression (5) is the value calculated by accumulating the opacities AU) provided from the expression (6) in accordance with the right side of the expression (5) up to the i-th voxel. In the expression (4), the accumulated value Aout(i−1) of the opacities up to the (i−1)-th voxel calculated as in the expression (5) is used. As apparent from the expression (5), Aout(i) is accumulated each time the voxel is passed, and is converged to 1.0. Thus, when the accumulated value Aout(i−1) of the opacities up to the (i−1)-th voxel is approximately 1.0 as shown in the above expression (4), the second term in the right side of the expression (4) is 0, and the elasticity value E(i) of the i-th and subsequent voxels is not reflected in the 2-dimensional projection image (3-dimensional) to be output. The initial values of Eout(i) and Aout(i) are zero.

S(i) in the expression (4) is a weight component for shading and is calculated from the slope of the elasticity value determined from the post-conversion elasticity value E(i) and its surrounding elasticity values. For example, when the normal line to the plane centered on the i-th voxel (slope of the elasticity value) matches the optical axis of a predefined light source, the light is reflected most strongly and thus 1.0 is provided as S(i) for the voxel i based on a predefined table and function. When the light source is orthogonal to the normal line, 0.0 is provided as S(i). This provides the shading for the obtained 2-dimensional projection image to achieve a highlighting effect. In addition, the slope (the normal-line direction) of the plane centered on the i-th voxel is calculated from the elasticity value or position of the i-th voxel and its surrounding voxels.

The method for providing hue information to an 3-dimensional elasticity image will be described later.

The multi-frame constituting unit (elasticity image) 48 generates a 2-dimensional elasticity image in an arbitrary cross-section from the pre-conversion elasticity volume data by the elasticity value converting unit 51. The specification of the arbitrary section is received by the interface unit 43 from the operator and is passed to the multi-frame constituting unit 48 through the image system control unit 44. A plurality of positions of the arbitrary cross-sections carne set, and the multi-frame constituting unit 48 generates the 2-dimensional elasticity image for each of the plural positions of the arbitrary cross-sections.

The switching and adding unit 12 is formed of a frame memory, an image processing unit, and an image selecting unit. The frame memory respectively stores the black and white tomographic images generated by the elasticity image constituting unit 7 and the multi-frame constituting unit 46, the color 2-dimensional elasticity image generated by the 2-dimensional elasticity image constituting unit 34 and the multi-frame constituting unit 48, the 3-dimensional image generated by the volume rendering unit 38, and the 3-dimensional elasticity image generated by the volume rendering unit 48.

The switching and adding unit 12 generates a combined image provided by adding the color 2-dimensional elasticity image to the black and white tomographic image at a predetermined ratio in response to an instruction of the operator. The black and white tomographic image generated by the elasticity image constituting unit 7 or the black and white tomographic image on the arbitrary cross-section generated by the multi-frame constituting unit 46 is used as the black and white tomographic image. The 2-dimensional elasticity image generated by the 2-dimensional elasticity image constituting unit 34 or the 2-dimensional elasticity image on the arbitrary cross-section produced by the multi-frame constituting unit 48 is used as the color 2-dimensional elasticity image. The known method of producing combined images of which the technique is disclosed in Patent Document 1 can be used for producing a composite image, by adding the output values of the respective pixels in the black and white tomographic image to the values in which the output values of the corresponding pixels in the color 2-dimensional elastic image is multiplied by a predetermined rate. The generated composite image is stored in the frame memory.

The switching and adding unit 12 selects and transfers the image to be displayed in the image display unit 13 from the monochrome section image, the color 2-dimensional elasticity image, the 3-dimensional image, the 3-dimensional elasticity image, and the combined image stored in the frame memory in response to an instruction received from the operator through the interface unit 43. The image display unit 13 displays the transferred one or more images in a predetermined arrangement on the screen.

The image system control unit 44 controls the respective components involved in the image production. The interface unit 43 receives the hue of the elasticity image (hue on the color map), the setting of an ROI (region of interest), the setting of the frame rate or the like from the operator. The image system control unit 44 displays the range of the elasticity values set for producing the 3-dimensional elasticity image, the color map for the elasticity image, the values of various set parameters and the like at predetermined positions on the screen in the image display unit 13.

Embodiment 1

Figure 3:
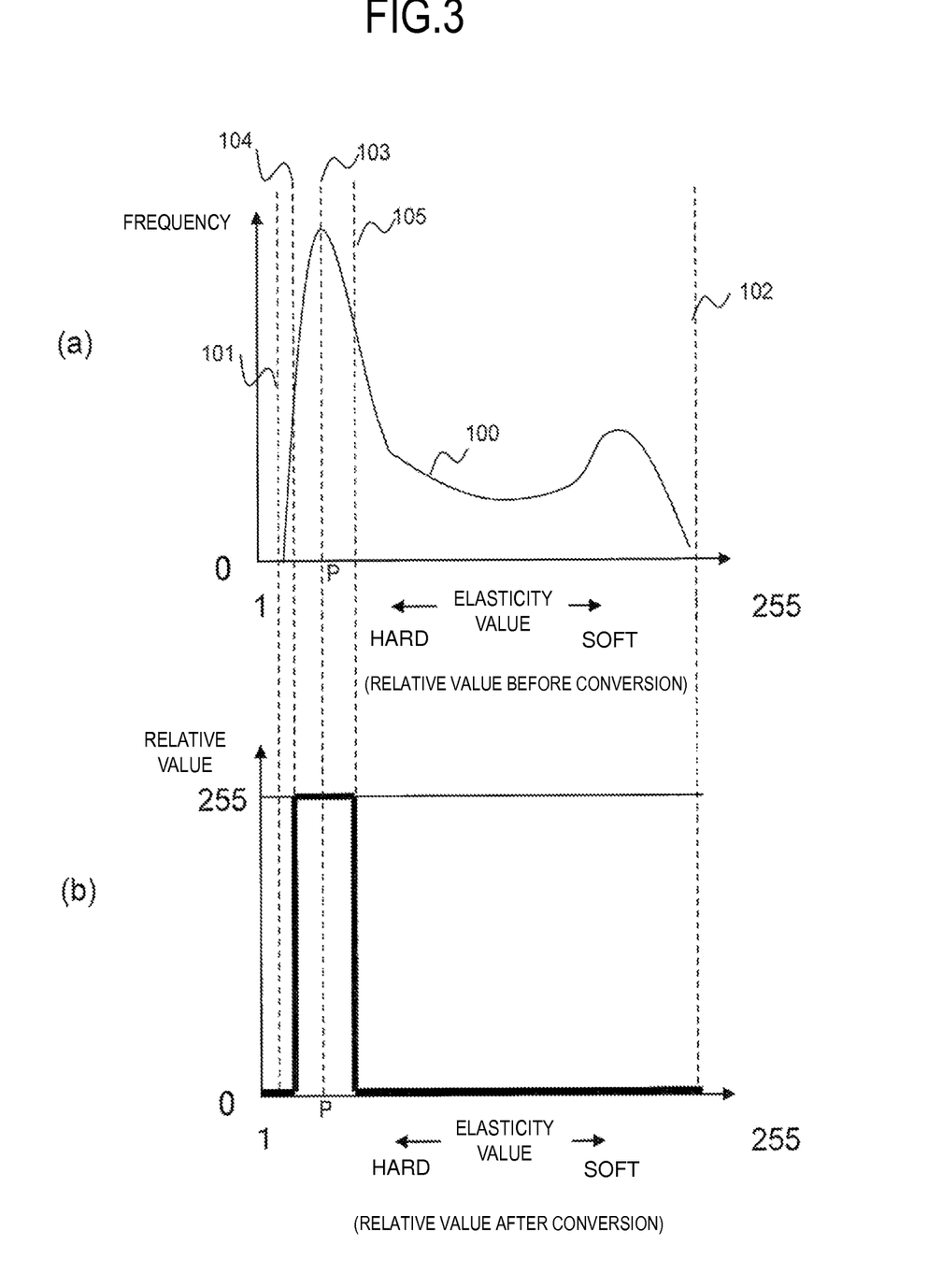
Figure 4:
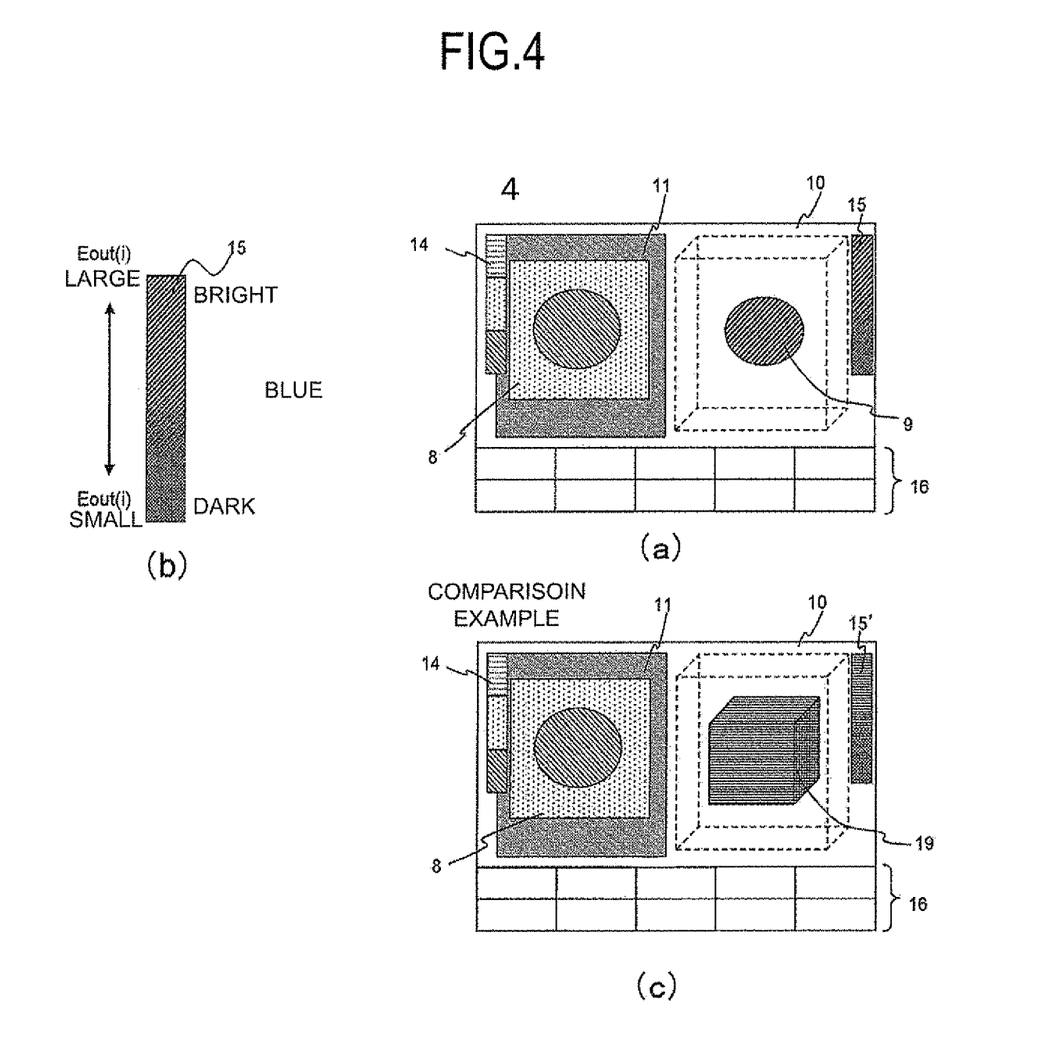

The operation of the elasticity value converting unit 51 in the first embodiment will be described referring to FIG. 2~FIG. 4.

Figure 2:
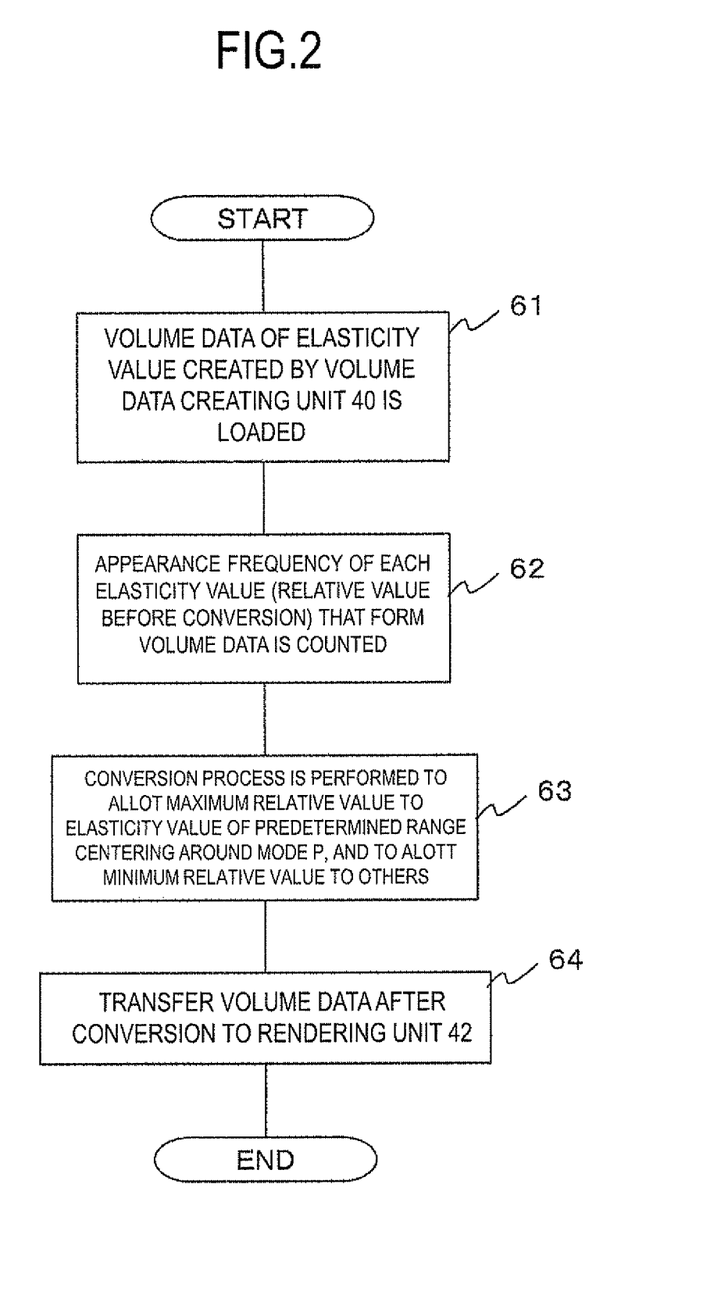
FIG. 2 is a flowchart showing the operation of the elasticity value converting unit in a first embodiment.

The elasticity value converting unit 51 performs the elasticity value conversion process as in the flowchart shown in FIG. 2 by reading in the program stored in the built-in memory. First, the elasticity value converting unit 51 takes in the volume data of the elasticity value which is generated by the volume data creating unit 36 in step 61 of FIG. 2. The pre-conversion volume data has configuration in which elasticity value 255 is allotted to the voxel having the largest relative value that represents the softest elasticity and relative value 1 is allotted to the voxel having the small elasticity value that indicates hard elasticity, wherein the relative value gradually changes in proportion to the elasticity value. That is, 255 levels of relative values are included in the elasticity value. In addition, in the case that no elasticity information is provided due to a noise or error, 0 is to be allotted to represent that no elasticity information is provided.

In step 62, the elasticity value converting unit 51 detects the elasticity value (pre-conversion relative value) of each voxel that constitutes the loaded volume data and the number thereof, and generates a graph 100 which represents the relationship between the elasticity values (pre-conversion relative values) and the frequency as shown in FIG. 3(a). In FIG. 3(a), a line 101 of the graph 100 indicates the hardest elasticity value (pre-conversion relative value) included in the volume data. A line 102 indicates the softest elasticity value (pre-conversion relative value) included in the volume data. A line 103 indicates the value with the highest frequency (mode value P) among the elasticity values (relative values) included in the volume data.

In step 63, as shown in FIG. 3(b), the elasticity value converting unit 51 executes conversion by allotting maximum value 255 as the post-conversion relative value with respect to the elasticity values (pre-conversion relative values) within a predetermined range with mode value P at its center, and allotting the minimum value as the post-conversion relative value to the elasticity values in the other range (pre-conversion relative values). The minimum value to be allotted may be 1 which indicates the minimum value of the elasticity value or 0 which indicates that there is no elasticity information, and an example in which 0 is allotted as the minimum value will be described below.

In concrete terms, as shown in FIG. 3(a), the elasticity value converting unit 51 calculates elasticity value (pre-conversion relative value) 104 of value P−k' which is smaller than mode value P by a portion of predetermined value k and elasticity value (pre-conversion relative value) 105 of a value P+k' which is larger than mode value P by a portion of k'. The elasticity value converting unit 51, as shown in FIG. 3(b), executes conversion by allotting maximum value 255 as the post-conversion relative value to the range which is from the elasticity value (pre-conversion relative value) 104 of P−k to the elasticity value (pre-conversion relative value) 105 of P+k' and allotting minimum value 0 to the other range as the post-conversion relative value. For example, k=10 and k'=10.

In this manner, volume data is generated in which a large value (maximum value 255) is given to the voxel corresponding to the elasticity values of a predetermined hardness with high appearance frequency, and a small value (minimum value 0) is given to voxels of the elasticity values with low appearance frequency in the other range. In step 64, the elasticity value converting unit 51 passes the post-conversion volume data to the volume rendering unit 42.

The volume rendering unit renders the post-conversion volume data using the above-described expressions (4)∼(6) to obtain Eout(i), so as to obtain a 3-dimensional elasticity image. The obtained 3-dimensional elasticity image is colored referring to the color map 15 for 3-dimensional elasticity images shown in FIG. 4(b).

The color map 15 for 3-dimensional images is a map for giving a hue (single color) corresponding to the pre-conversion elasticity value range in which the elasticity value converting unit 51 provided maximum value 255 (elasticity values in a prescribed range with mode value P at its center), and for changing the luminance (brightness) in accordance with the magnitude of the value of Eout(i). As the contribution of the weight component S(i) for shading is larger (S(i) is smaller) in the expression (4), Eout(i) is smaller and thus the setting is performed to be closer to black (lower luminance). By performing the setting to be closer to black (lower luminance) as the contribution of S(i) in the expression (4) is larger, that is, as the value of Eout(i) is smaller, the shading effect can be achieved to result in the stereoscopic three-dimensional elasticity image.

A hue (single color) corresponding to the pre-conversion elasticity value is set, for example, as blue when the predetermined value from among the average value, maximum value or minimum value of the pre-conversion elasticity values in the predetermined range with mode value P at its center is smaller than average value 127 of all the elasticity values, and as red when it is larger. Or, the hue may be set, in the color map 14 of a 2-dimensional elasticity image, to correspond with a predetermined value from among the average value, maximum value or minimum value of the pre-conversion elasticity values in a predetermined range with mode value P at its center.

In the present first embodiment, it is possible to obtain a 3-dimensional elasticity image of tissue having noteworthy hardness with high frequency (the range of post-conversion large elasticity values), since the relative value of the soft tissue is 0 in the post-conversion volume data in the elasticity value converting unit 51 and is not depicted in the 3-dimensional elasticity image. Furthermore, the voxel of the hard tissue with high frequency has a post-conversion large relative value, thus the values after being integrated become large to result in the acquisition of a clear 3-dimensional elasticity image with high contrast.

The obtained 3-dimensional image is displayed on the image display unit 13 via the switching and adding unit 12. FIG. 4(a) is an example of an image to be displayed on the image display unit 13. A 3-dimensional elasticity image 9 is displayed in the right-side region on a screen 10. The 3-dimensional elasticity image 9 is of hard tissue with high frequency which is converted into a large relative value. On the right side of the 3-dimensional elasticity image 9, the color map 15 for 3-dimensional elasticity images is displayed showing the relationship between the color of the 3-dimensional elasticity image 9 and the elasticity value.

On the left side of the screen 10, a composite image of the black and white tomographic image 11 and a 2-dimensional elasticity image 8 is displayed. Since the 2-dimensional elasticity image 8 is generated only in an ROI set by an operator, only the region in the central part of the display region is synthesized in the black and white tomographic image. On the left side of the 2-dimensional elasticity image 8, the color map 14 is displayed showing the relationship between the color of the 2-dimensional elasticity image 8 and the elasticity value. Since the 2-dimensional elasticity image 8 is generated from the pre-conversion data by the elasticity value converting unit 51, the color map 14 is provided respectively with red in the soft region with large elasticity values, blue in the hard region with small elasticity values, and green in the intermediate region. Each color is changed in incremental steps according to the value of elasticity, and 256 levels of gradation is provided in the entire map. In addition, the values of various parameters received from the operator are displayed in a region 16 in the lower part of the screen 10.

The present first embodiment includes the elasticity image volume data creating unit 40 configured to create volume data constituted by elasticity value data which represents elasticity using the signals received by transmitting ultrasonic waves to the inside of the object 1, the elasticity value converting unit 51 configured to count the frequency of the elasticity value data which constitutes volume data for each magnitude of the elasticity value and converts the elasticity values within a predetermined range based on the frequency into a large value and the elasticity values outside the predetermined range into a small value, and the volume rendering unit 42 configured to generate a 3-dimensional elasticity image by rendering the volume data which is after converted in the elasticity value converting unit 51.

The elasticity value converting unit 51 binarizes the elasticity values by converting the elasticity values within a predetermined range which is defined on the basis of the frequency into a first constant and the elasticity values that are outside the predetermined range into a second constant which is smaller than the first constant. The above-described predetermined range of the elasticity value can include the elasticity value with the highest frequency.

As apparent from FIG. 4(a), the 3-dimensional elasticity image 9 of hard tissue with high frequency which is covered by soft tissue can be clearly depicted. Therefore, the operator can identify that there is hard tissue inside of soft tissue by confirming the composite image of the black and white tomographic image 11 and the 2-dimensional elasticity image 8, and identify the 3-dimensional form of the hard tissue with high frequency by observing the 3-dimensional elasticity image 9 at the same time, which can result in visible recognition of the 3-dimensional elasticity image of noteworthy hard tissue such as a tumor.

As a comparative example, a 3-dimensional elasticity image 19 is shown in FIG. 4(c), which is obtained by rendering the pre-conversion elasticity volume data by the elasticity value converting unit 51 using the expressions (4)~(6). Since the elasticity value (relative value) of hard tissue is small and the elasticity value (relative value) of soft tissue which covers the hard tissue is large in volume data, when the elasticity values of the voxels on the line of sight are sequentially integrated by rendering, the contribution rate of the voxel with a large and soft elasticity value to the 2-dimensional projection plane becomes high, thus the 3-dimensional elasticity image 19 in which the outward form of the soft tissue is depicted is obtained as shown in FIG. 4(c). Consequently, the image of noteworthy hard tissue which is inside of the soft tissue cannot be identified in FIG. 4(c).

While the maximum value is given to the range from P–k to P+k centering on mode value P in the first embodiment, the setting of the range for providing the maximum value may be performed by the operator via the interface unit. Also, the range may be set using a statistic such as dispersion. The range may also be set with a statistic other than mode value P such as the average value, the maximum value or the minimum value at its center. The elasticity values in the predetermined range defined on the basis of the frequency may also include the values defined using any of the mode value, average value, maximum value or minimum value of the elasticity values which constitute the volume data and is acquired based on the frequency for each magnitude of the elasticity value. For example, the elasticity value within a predetermined range defined on the basis of the frequency is the minimum value of the elasticity values which constitute the volume data and is obtained by the frequency for each magnitude of the elasticity value, and the elasticity value converting unit 51 allots a predetermined large value to the minimum value of the elasticity values and allots progressively smaller values than the predetermined large value as the elasticity values that constitute the volume data become larger.

Also, while elasticity values are binarized in the present embodiment by giving maximum value 255 to a predetermined range and giving the minimum value 0 to the values in the other range, the two values to be given may not be 0 and 255, but any two values having a sufficient difference between them.

Further, it is also possible, by dividing the elasticity values of the volume data in advance into plural regions, to perform rendering on each divided region by converting the elasticity values by the first embodiment.

Embodiment 2

Next, the operation of the elasticity value converting unit 51 in the second embodiment will be described using FIG. 5 and FIG. 6.

In the second embodiment, the elasticity value converting unit 51 performs conversion by allotting the largest relative value to mode value P from among the elasticity values and allotting the relative values to be linearly smaller to the elasticity values in the range which is larger or smaller than the mode value P. In other words, the elasticity value converting unit 51 converts the elasticity values in the range which is determined on the basis of the frequency into a first constant, and converts the elasticity values in the range other than the predetermined range into the values which progressively become smaller than the first constant as they get farther away from the elasticity values in the predetermined range.

First, the elasticity value converting unit 51 carries out steps 61 and 62 in FIG. 2 of the first embodiment, and creates a graph 200 which represents the relationship between the elasticity values (pre-conversion relative values) and the frequency with respect to the volume data output from the elasticity value volume data creating unit 40 as shown in FIG. 5(a). A line 201 indicated in the graph 200 represents the hardest elasticity value (pre-conversion relative value) included in the volume data. A line 202 represents the softest elasticity value (pre-conversion relative value) included in the volume data. A line 203 represents the value with the highest frequency (mode value P) among the elasticity values (pre-conversion relative value) included in the volume data.

In the second embodiment, the process of converting the relative values is performed in step 63 as shown in FIG. 5(b). That is, the elasticity value converting unit 51 allots 255 as the post-conversion relative value to mode value P which is denoted by the line 203, and allots 0 to the hardest elasticity value (pre-conversion relative value) which is denoted by the line 201. To the elasticity values between the line 203 and the line 201, the post-conversion relative values are allotted so that the post-conversion relative values become progressively smaller as the elasticity values (pre-conversion relative values) become smaller. In the same manner, to the elasticity values between the line 203 to the line 202, the post-conversion relative values are allotted so that the post-conversion relative values become progressively smaller as the pre-conversion elasticity values (relative values) become larger.

In this way, the maximum relative value 255 is given to the voxel corresponding to the hard elasticity value with the highest appearance frequency in the volume data, and the relative values which become smaller as they get farther apart from the elasticity value of the mode value are given to the voxels of the elasticity values in the ranges other than the mode value, with the mode value at their center. The minimum value and the maximum value in the elasticity values have the minimum relative value 0.

In step 64, the elasticity value converting unit 51 transfers the post-conversion volume data to the volume rendering unit 42. The volume rendering unit 42 renders the post-conversion volume data using the above-mentioned expressions (4)~(6) to obtain a 3-dimensional elasticity image.

Figure 6:
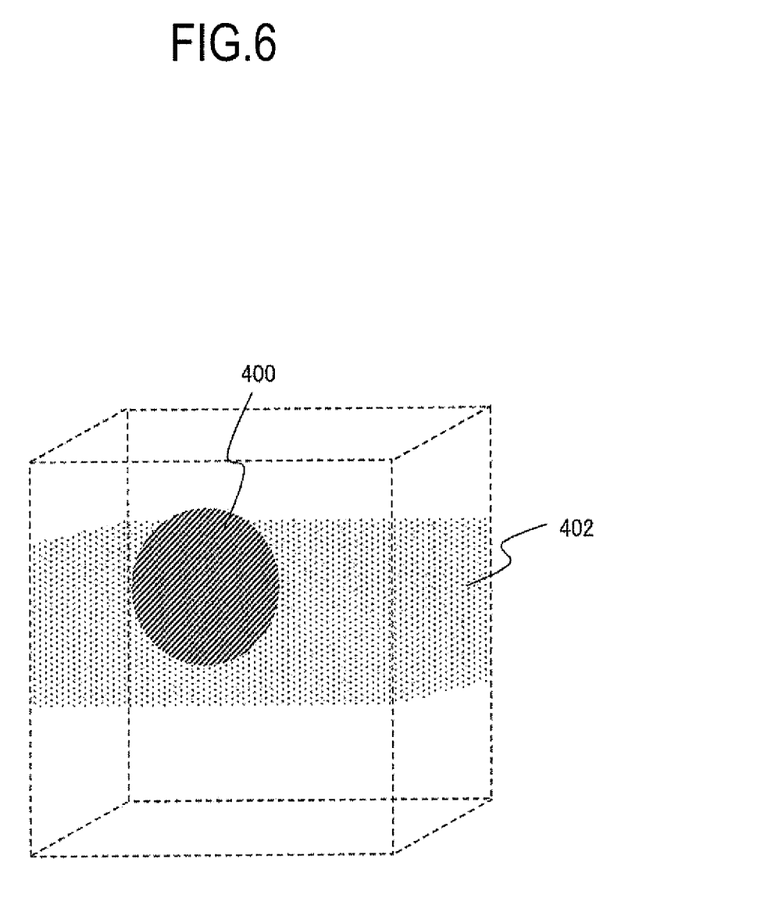
FIG. 6 is an explanatory diagram showing a 3-dimensional elasticity image which is obtained in the second embodiment.

An example of the obtained 3-dimensional elasticity image is shown in FIG. 6. In the present second embodiment, since the conversion is performed so that a large relative value is allotted to the tissue with the high frequency of the elasticity values and the relative values progressively vary with the mode value at their center, it is possible to clearly depict a 3-dimensional elasticity image 400 of noteworthy hard tissue with high frequency (the range of post-conversion large elasticity values) with high contrast. Furthermore, since the post-conversion relative values of the soft values with low frequency are not 0, a 3-dimensional elasticity image 402 of the soft tissue with low frequency is depicted around the 3-dimensional elasticity image 400 of the hard tissue by rendering, as shown in FIG. 6. Since the relative values of the soft tissue with low frequency is small and the values thereof after being integrated by rendering also become small, thus the 3-dimensional elasticity image 402 of the soft tissue with low frequency becomes the image with low contrast. In this manner, as shown, in FIG. 6, it is possible to confirm the 3-dimensional form of the 3-dimensional elasticity image 400 representing hard tissue with high frequency without being covered by the 3-dimensional elasticity image of soft tissue with low frequency, while identifying the 3-dimensional form of the soft tissue at the same time.

As described above, in accordance with the present second embodiment, an operator can identify both a 3-dimensional elasticity image of noteworthy hard tissue such as a tumor and a 3-dimensional elasticity image of soft tissue at the same time.

While the conversion is performed in the second embodiment such that the post-conversion relative values progressively become smaller with the mode value at their center, the center value is not limited to the mode value. The center value can also be calculated with reference to a statistical value such as the average value, maximum value or minimum value.

While the maximum value of the post-conversion relative values is set as 255 in the second embodiment, a predetermined value may also be smaller than 255.

Figure 5:
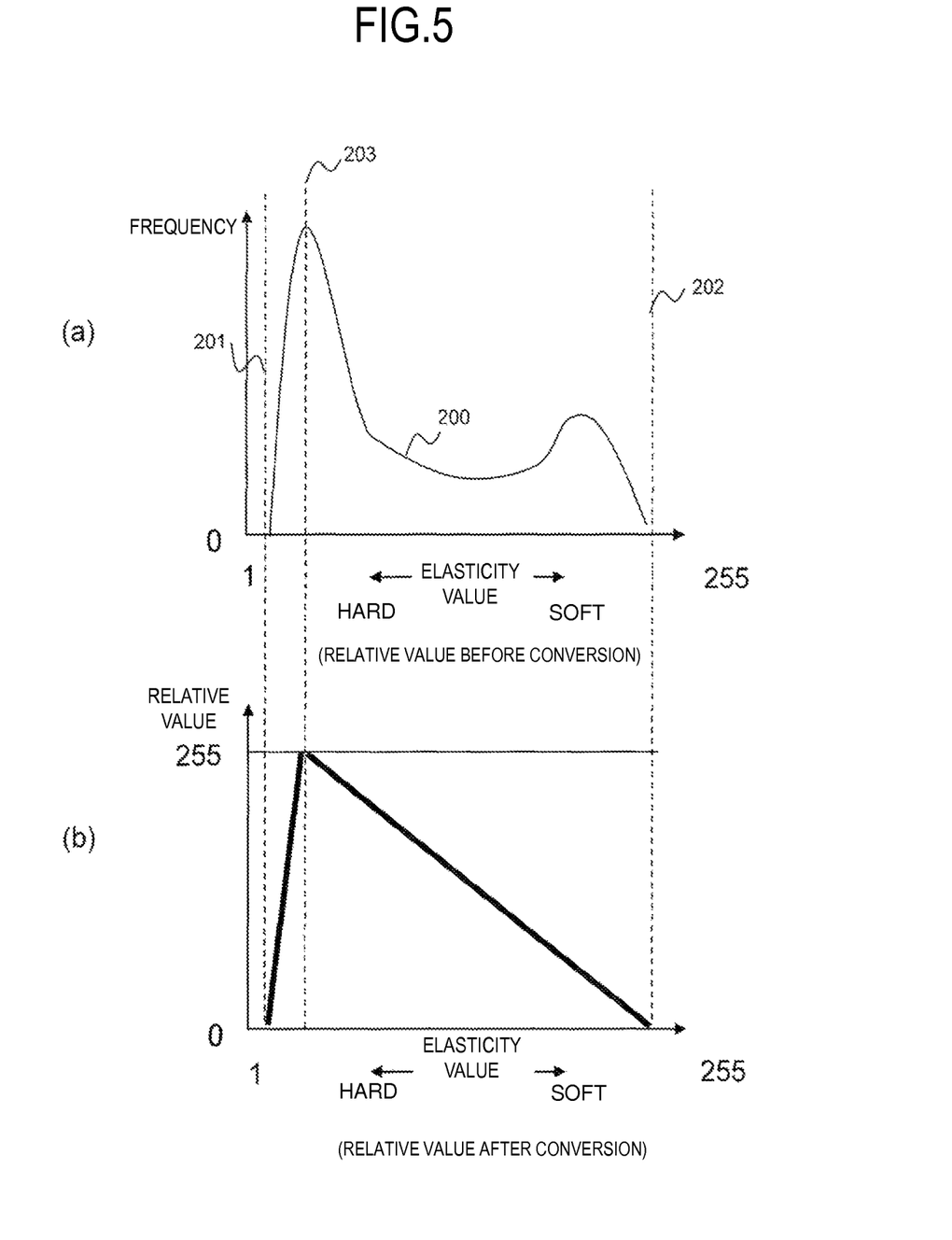

Also, while conversion is performed in the second embodiment such that the post-conversion relative values linearly become smaller with the central value at their center as shown in FIG. 5, the pattern of value variation is not limited to linear, and the relative values may also become smaller progressively, for example in a curved or stepped pattern.

Furthermore, by dividing the elasticity values of volume data in advance into plural regions, rendering can be performed by converting the elasticity values by the second embodiment for each divided region.

Embodiment 3

Figure 7:
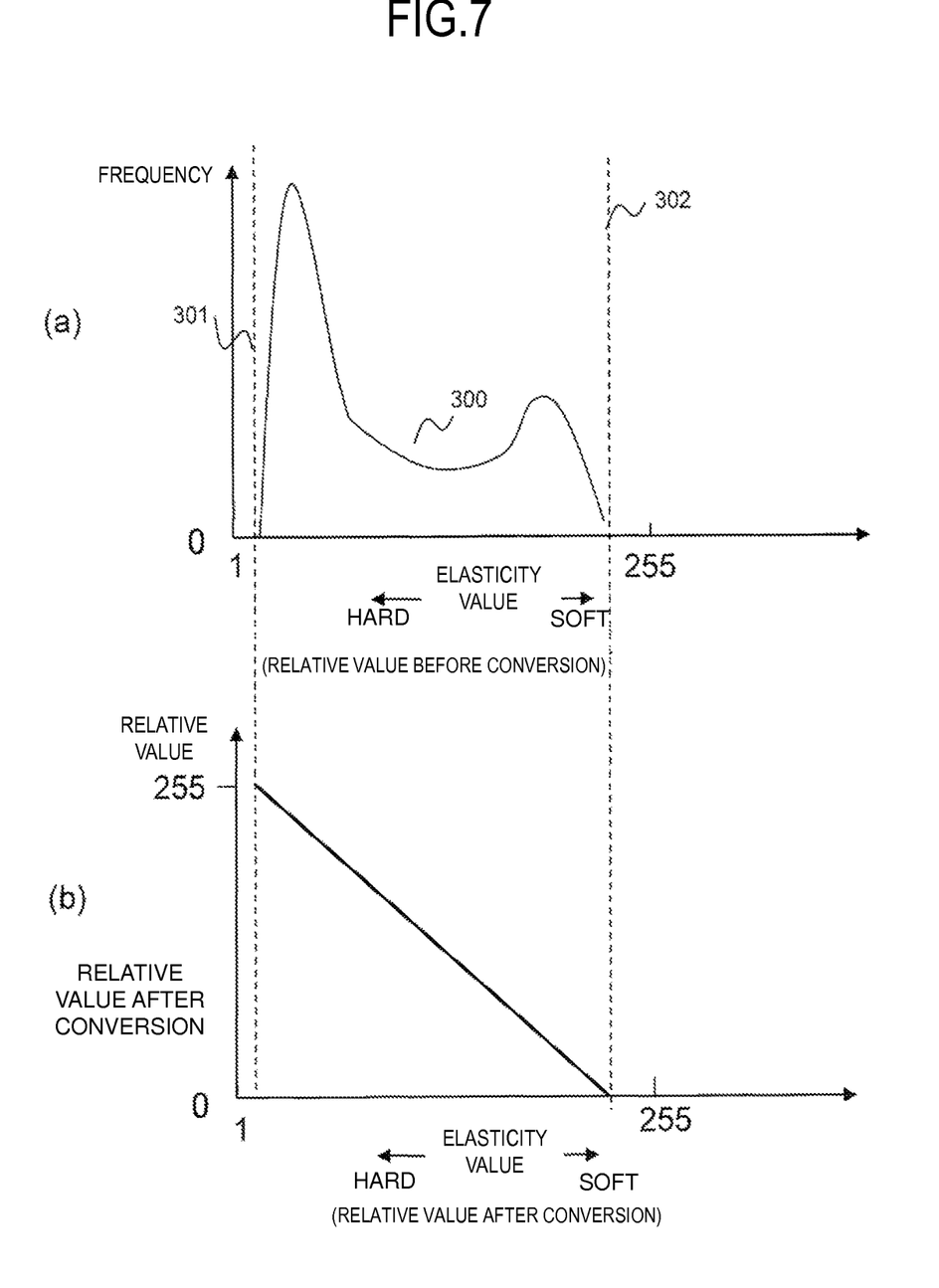

Next, the operation of the elasticity value converting unit 51 in the third embodiment will be described referring to FIG. 7. In the third embodiment, the elasticity value converting unit 51 performs conversion such that the maximum relative value 255 is allotted to the smallest elasticity value (the hardest tissue) from among the elasticity values (pre-conversion relative values) that constitute the volume data, the smallest relative value 0 is allotted to the largest elasticity value (the softest tissue), and the relative values are allotted to be linearly smaller in accordance with the elasticity value to the elasticity value range between the minimum and the maximum elasticity values.

The elasticity value converting unit 51 creates a graph 300 which represents the relationship between the elasticity values (pre-conversion relative value) and the frequency in the pre-conversion volume data as shown in FIG. 7(a), by executing steps 61 and 62 in the first embodiment shown in FIG. 2. A line 301 indicates the minimum (hard) elasticity value included in the elasticity volume data. A line 302 indicates the maximum (soft) elasticity value included in the elasticity volume data.

In step 63, the elasticity value converting unit 51 extracts the elasticity values (pre-conversion relative values) on lines 301 and 302, and provides the maximum value 255 to the smallest (hard) elasticity value (line 301) as the post-conversion relative value, as shown in FIG. 7(b). The minimum value 0 is provided to the maximum (soft) elasticity value (line 302) as the post-conversion relative value. The elasticity values between the line 301 and the line 302 are linearly varied. The rest of the configuration is the same as the first embodiment.

In this manner, hard tissue can be converted into a large elasticity value (post-conversion relative value) and soft tissue can be converted into a small elasticity value (post-conversion relative value), as well as the maximum value 255 can be given to the hardest tissue and the minimum value 0 can be given to the softest tissue, so as to optimize the gradation of the relative values.

Since a 3-dimensional elasticity image obtained in the third embodiment is generated such that a large elasticity value (post-conversion) is given to noteworthy hard tissue such as a tumor, it is possible to depict a 3-dimensional elasticity image of the hard tissue with high contrast. Moreover, since the post-conversion relative value of the soft tissue is not 0, a 3-dimensional elasticity image thereof can also be depicted though with low contribution rate. In this manner, both the 3-dimensional form of the hard region and the 3-dimensional form of the soft region can be identified at the same time.

It also is possible to divide the elasticity values of the volume data into plural regions in advance and convert the respective divided regions in order to perform rendering.

Embodiment 4

Figure 8:
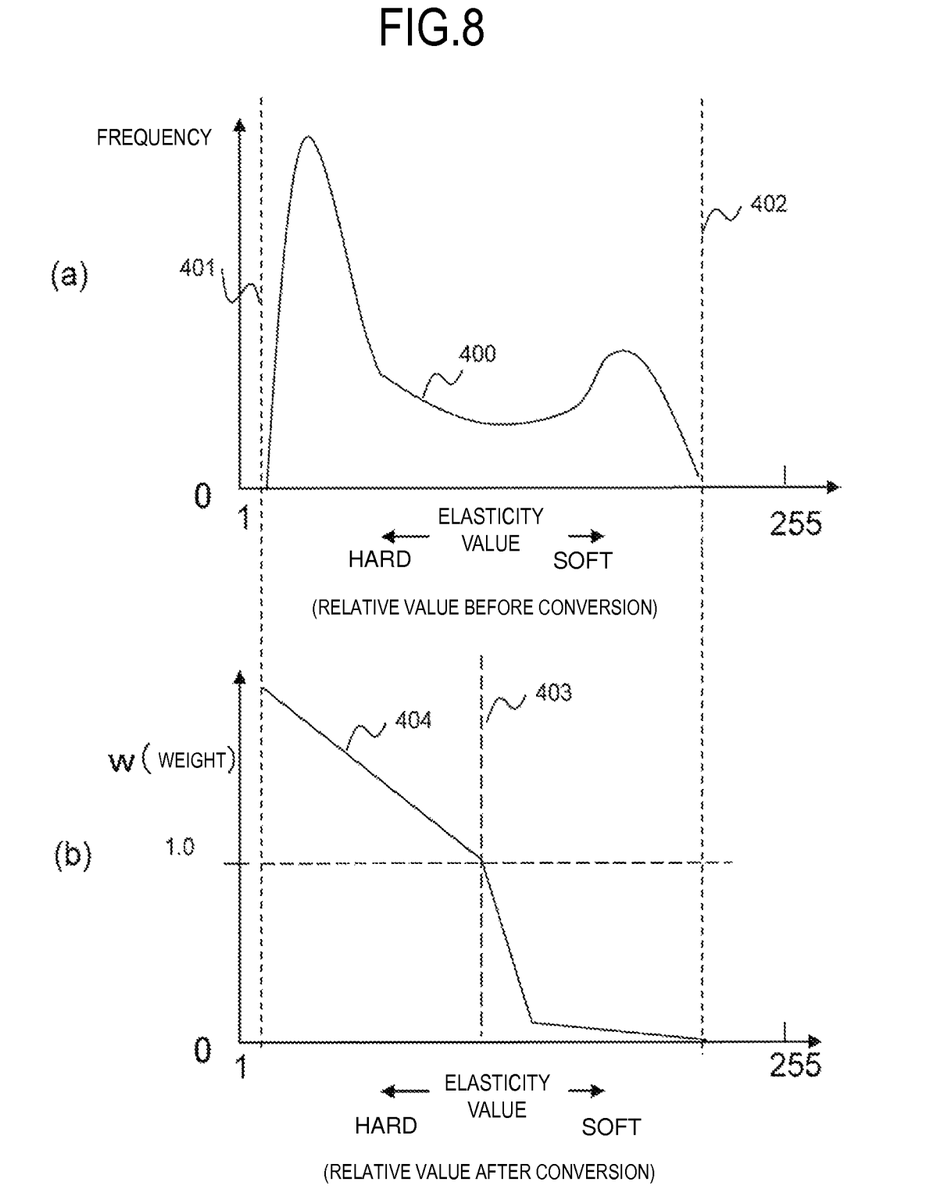

Next, the operation of the elasticity value converting unit 51 in the fourth embodiment will be described referring to FIG. 8. In the fourth embodiment, predetermined small values (hard tissue) from among the elasticity values (pre-conversion relative values) that constitute the volume data are converted into a large value by multiplying weight w (w>1).

Large elasticity values (soft tissue) are converted into a small value by multiplying weight w (w<1).

The elasticity value converting unit 51 carries out steps 61 and 62 in FIG. 2 of the first embodiment, and creates a graph 300 which represents the relationship between the elasticity values (pre-conversion relative values) and the frequency with respect to the pre-conversion volume data as shown in FIG. 8(a). A line 401 represents the minimum (hard) elasticity value included in the elasticity volume data. A line 402 represents the maximum (soft) elasticity value included in the elasticity volume data.

In step 63, the elasticity value converting unit 51 extracts the elasticity value (pre-conversion relative value) of the lines 401 and 402, and calculates the average value of all the elasticity values that constitute the volume data. A line 403 in FIG. 8(b) indicates the obtained average value.

The elasticity value converting unit 51 generates weight w which is a function of the elasticity values as shown in FIG. 8(b). Weight w is generated to be 1 for the average value of the elasticity values, to be w>1 in the range from the minimum (hard) elasticity value (line 401) to the average value (line 403), and to be w<1 in the range from the maximum (soft) elasticity value (line 402) to the average value (line 403). That is, the elasticity value converting unit 51 obtains the average value, maximum value and minimum value of the elasticity values which constitute the volume data, from the frequency of each magnitude of the elasticity value, and converts the elasticity values by multiplying weight 1 by the elasticity value of the average value, multiplying the weight which is larger than 1 by the elasticity values from the minimum value to the average value, and multiplying the weight which is smaller than 1 by the elasticity values from the average value to the maximum value.

For example, weight w can be set to be 255 when the elasticity value (line 401) of the minimum value (the hardest)

is multiplied by weight w. Also, weight w of the elasticity value (line 402) of the maximum value (the softest) can be set as 0. The straight line or the curve line to connect these weight values and weight w=1 of the average value (line 403) can be set to be a predetermined form of line.

The elasticity value converting unit 51 generates the post-conversion volume data by multiplying the function of the generated weight w by the elasticity values (pre-conversion) that constitute the volume data. In this manner, the elasticity value of hard tissue is converted into a large value and the elasticity value of the soft tissue is converted into a small value. Also, maximum value 255 can be given to the hardest tissue and minimum value 0 can be given to the softest tissue, so that the gradation of the relative values can be optimized.

In 3-dimensional elasticity images which can be obtained in the fourth embodiment, a large elasticity value (post-conversion) is given to hard tissue with high frequency which is noteworthy to be depicted, so that the 3-dimensional elasticity image of the hard tissue with high frequency can be clearly depicted with high contrast. Moreover, since the post-conversion relative value of soft tissue with low frequency is not 0, a 3-dimensional elasticity image of the soft tissue can also be depicted though with low contribution rate. In this manner, both of the 3-dimensional shape of hard tissue and the 3-dimensional shape of soft tissue can be identified at the same time.

It also is possible to divide the elasticity values of the volume data into plural regions in advance and convert the elasticity values in the respective regions by means of the third embodiment, so that the volume rendering unit can perform rendering on each divided region.

In addition, while the case that the elasticity values of the entire volume data are converted has been described in the first~fourth embodiments, it is also possible to convert the elasticity values of a partial region in the elasticity volume data.

Also, the case that the elasticity values are converted after generation of the volume data is exemplified in the first~fourth embodiments, the elasticity volume data may also be created after performing the conversion of the present embodiment with respect to the output of the 2-dimensional elasticity image constructing unit 34 before the volume data is generated.

DESCRIPTION OF REFERENCE NUMERALS 1 object
2 probe
3 transmission unit
4 reception unit
5 ultrasonic transmission/reception control unit
6 phasing and adding unit
7 tomographic image constructing unit
8 color 2-dimensional elasticity image
9 3-dimensional elasticity image
10 screen
11 black and white tomographic image
12 switching and adding unit
13 image display unit
14 color map (2-dimensional elasticity image)
15 color map (3-dimensional elasticity image)
16 parameter display area
27 RF signal frame data storing unit
28 RF signal frame data selecting unit
30 displacement measuring unit
32 elasticity information calculating unit
34 2-dimensional elasticity image constructing unit
36 tomographic image volume data creating unit
38 volume rendering unit
39 2-dimensional elasticity image storing unit
40 elasticity image volume data creating unit
42 volume rendering unit
43 interface unit
44 image system control unit
45 minor-axis scan position control unit
46 multi-frame constructing unit (tomographic image)
48 multi-frame constructing unit (elasticity image)
51 elasticity value converting unit

The invention claimed is:

1. An ultrasonic diagnostic apparatus comprising:
an elasticity image volume data creating unit configured to generate volume data constituted by elasticity value data which represents the elasticity using the signals that are received by transmitting ultrasonic waves to the inside of an object to be examined;
an elasticity value converting unit configured to count the frequency with respect to the elasticity value data which constitute the volume data for each magnitude of the elasticity value, and converts the elasticity values in a prescribed range which is determined by the frequency into a large value and the elasticity values outside the prescribed range into a small value; and
a volume rendering unit configured to generate a 3-dimensional elasticity image by rendering the post-conversion volume data in the elasticity value converting unit.

2. The ultrasonic diagnostic apparatus according to claim 1, wherein the elasticity value converting unit performs binarization by converting the elasticity values in a prescribed range which is determined on the basis of the frequency into a first constant and the elasticity values outside the prescribed range into a second constant which is smaller than the first constant.

3. The ultrasonic diagnostic apparatus according to claim 1, wherein the elasticity value converting unit converts the elasticity values in a prescribed range which is determined on the basis of the frequency into a first constant, and converts the elasticity values outside the prescribed range to be progressively smaller than the first constant as the they get farther away from the elasticity values in the prescribed range.

4. The ultrasonic diagnostic apparatus according to claim 1, wherein the elasticity values in a prescribed range based on the frequency include the elasticity value with the highest frequency.

5. The ultrasonic diagnostic apparatus according to claim 1, wherein the elasticity values in a prescribed range which are determined based on the frequency include the values determined by using any of the mode value, the average value, the maximum value or the minimum value of the elasticity values that constitute the volume data, which are acquired based on the frequency for each magnitude of the elasticity value.

6. The ultrasonic diagnostic apparatus according to claim 1, wherein:
the elasticity value in a prescribed range which is determined based on the frequency is the minimum value of the elasticity values that constitute the volume data, and is calculated based on the frequency for each magnitude of the elasticity value; and
the elasticity value converting unit allots a prescribed large value to the maximum value of the elasticity value, and allots progressively smaller values than the prescribed large value as the elasticity values that constitute the volume data become larger.

7. The ultrasonic diagnostic apparatus according to claim 1, wherein the elasticity value converting unit acquires the average value, the maximum value and the minimum value of the elasticity values that constitute the volume data and are calculated based on the frequency for each magnitude of the elasticity value, and converts the elasticity values by multiplying the elasticity value of the average value by weight 1, the elasticity values from the minimum value to the average value by the weight which is larger than 1, and the elasticity values from the average value to the maximum value by the weight which is smaller than 1.

8. The ultrasonic diagnostic apparatus according to claim 1, wherein the maximum value and the minimum value of the post-conversion volume data in the elasticity value converting unit can be rendered by the volume rendering unit respectively.

9. The ultrasonic diagnostic apparatus according to claim 1, wherein the volume rendering unit divides elasticity values in the volume data into plural regions in advance and executes rendering by performing conversion of the elasticity values in each divided region.

10. The ultrasonic diagnostic apparatus according to claim 1, wherein the elasticity value converting unit converts the elasticity values having a prescribed small value among the elasticity values that constitute the volume data into a large value by applying weighting to the elasticity value.

11. The ultrasonic diagnostic apparatus according to claim 1, wherein the elasticity value converting unit performs conversion by allotting the maximum relative value to the mode value among the elasticity values and allotting the relative values to be linearly smaller to the elasticity values in the ranges which are larger and smaller than the mode value.

12. The ultrasonic diagnostic apparatus according to claim 1, wherein the elasticity value converting unit performs conversion, in the elasticity values that constitute the volume data, by allotting the largest relative value to the maximum elasticity value, the smallest relative value to the minimum elasticity value, and the relative values to be linearly smaller in accordance with the elasticity value to the elasticity values in the range between the maximum elasticity value and the minimum elasticity value.

13. An ultrasonic image display method comprising:
generating volume data constituted by elasticity value data that represents elasticity using signals received by transmitting ultrasonic waves to the inside of an object to be examined,
counting the frequency of the elasticity value data that constitutes the volume data for each magnitude of the elasticity value,
converting the elasticity values in a prescribed range which is determined on the basis of the frequency into a large value and the elasticity values outside the prescribed range into a small value, and
generating and displaying a 3-dimensional elasticity image by rendering the post-conversion volume data.

* * * * *